US006972012B1

(12) United States Patent
Pozniak et al.

(10) Patent No.: US 6,972,012 B1
(45) Date of Patent: Dec. 6, 2005

(54) PANT-LIKE DISPOSABLE ABSORBENT ARTICLES

(75) Inventors: Jennifer Elizabeth Pozniak, Appleton, WI (US); Timothy James Blenke, Neenah, WI (US); Cassandra Elizabeth Morris, Charlottesville, VA (US); Thomas Harold Roessler, Menasha, WI (US); Jody Dorothy Suprise, Pine River, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/706,294

(22) Filed: Nov. 3, 2000

Related U.S. Application Data (63) Continuation-in-part of application No. 09/216,545, filed on Dec. 18, 1998.

(51) Int. Cl.⁷ .............................................. A61F 13/15
(52) U.S. Cl. ...................................... 604/386; 604/391
(58) Field of Search .......................... 604/385.01, 389, 604/391, 390, 386

(56) References Cited

U.S. PATENT DOCUMENTS

| 1,079,479 | A | 11/1913 | Earnshaw |
| 1,485,001 | A | 2/1924 | Wills |
| 1,657,909 | A | 1/1928 | Abramovich |
| 1,705,194 | A | 3/1929 | Marinsky |
| 1,762,468 | A | 6/1930 | Brewer |
| 1,963,334 | A | 6/1934 | Neilson |
| 2,201,255 | A | 5/1940 | Wilson, Jr. |
| 2,242,977 | A | 5/1941 | Marcos |
| 2,475,175 | A | 7/1949 | Cadous |
| 2,477,914 | A | 8/1949 | Webb |
| 2,545,761 | A | 3/1951 | Brink |
| 2,570,963 | A | 10/1951 | Mesmer |
| 2,630,120 | A | 3/1953 | Nielson |

(Continued)

FOREIGN PATENT DOCUMENTS

AU              667899           4/1996

(Continued)

OTHER PUBLICATIONS

Derwent World Patent Database abstract of FR 2762507 A1: Description of RAHALA, "Baby's Disposable Nappy."

(Continued)

*Primary Examiner*—Larry I. Schwartz
*Assistant Examiner*—C. Lynne Anderson
(74) *Attorney, Agent, or Firm*—David J. Klann (57) ABSTRACT

A pant-like, refastenable, disposable absorbent article includes an absorbent chassis, a pair of opposed side panels, a pair of releasable joints and a pair of proportional fasteners. The absorbent chassis defines a pair of laterally opposed side edges and a pair of longitudinally opposed waist edges. The side panels extend between and connect the side edges of the absorbent chassis to define a waist opening and a pair of leg openings in the pant-like disposable absorbent article. Each of the opposed side panels defines a first side margin which is permanently attached to the side edge of the absorbent chassis in one waist region of the absorbent article to provide a permanent joint. Each of the opposed side panels further defines a second side margin opposite the first side margin which is releasably attached to the side edges of the absorbent chassis in the other waist region of the absorbent article to provide the releasable joints. The proportional fasteners are located adjacent the releasable joints and are configured to be smaller in the longitudinal direction than the releasable joints. The fasteners are used to refastenably engage the second side margins of the side panels to the opposite waist region of the absorbent article.

8 Claims, 5 Drawing Sheets

U.S. PATENT DOCUMENTS

| | | |
|---|---|---|
| 2,630,806 A | 3/1953 | Kiscaden |
| 2,743,725 A | 5/1956 | Metthews |
| 2,801,632 A | 8/1957 | Burner et al. |
| 2,808,831 A | 10/1957 | Winslett |
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Sr. |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A | 5/1988 | Cole |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,065 A * | 5/1991 | Scripps ................. 604/385.21 |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A | 12/1991 | Davis |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A | 1/1993 | Roessler et al. |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A * | 12/1994 | Ando et al. ................. 604/358 |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |
| 5,489,282 A | 2/1996 | Zehner et al. |
| 5,496,298 A | 3/1996 | Kuepper et al. |
| 5,499,978 A | 3/1996 | Buell et al. |
| 5,500,063 A | 3/1996 | Jessup |
| 5,509,915 A | 4/1996 | Hanson et al. |
| 5,527,302 A | 6/1996 | Endres et al. |
| H1558 H | 7/1996 | Goulait et al. |
| 5,531,731 A | 7/1996 | Brusky |
| 5,531,732 A | 7/1996 | Wood |
| 5,537,722 A | 7/1996 | Niederhofer et al. |
| 5,540,796 A | 7/1996 | Fries |
| 5,545,158 A | 8/1996 | Jessup |
| 5,545,275 A | 8/1996 | Herrin et al. |
| 5,549,592 A * | 8/1996 | Fries et al. ................. 604/386 |
| 5,554,146 A | 9/1996 | Niederhofer et al. |

| | | | | | | |
|---|---|---|---|---|---|---|
| 5,562,650 A | 10/1996 | Everett et al. | | 6,447,497 B1 * | 9/2002 | Olson .................. 604/389 |
| 5,569,232 A | 10/1996 | Roe et al. | | 6,524,293 B1 | 2/2003 | Elsberg et al. |
| 5,569,234 A | 10/1996 | Buell et al. | | | | |
| 5,571,586 A | 11/1996 | Gobran | | | | |

FOREIGN PATENT DOCUMENTS

| | | |
|---|---|---|
| 5,575,784 A | 11/1996 | Ames-Ooten et al. |
| 5,582,606 A | 12/1996 | Bruemmer et al. |
| 5,591,152 A | 1/1997 | Buell et al. |
| 5,593,401 A | 1/1997 | Sosalla et al. |
| 5,601,546 A | 2/1997 | Tanji et al. |
| 5,605,735 A * | 2/1997 | Zehner et al. .............. 428/100 |
| 5,607,416 A | 3/1997 | Yamamoto et al. |
| 5,611,789 A | 3/1997 | Seth |
| 5,618,366 A | 4/1997 | Suekane |
| 5,624,420 A | 4/1997 | Bridges et al. |
| 5,624,424 A | 4/1997 | Saisaka et al. |
| 5,624,428 A | 4/1997 | Sauer |
| 5,624,429 A * | 4/1997 | Long et al. .................... 2/912 |
| 5,626,574 A | 5/1997 | Sasaki et al. |
| 5,628,738 A | 5/1997 | Suekane |
| 5,629,063 A | 5/1997 | Gobran |
| 5,634,916 A | 6/1997 | Lavon et al. |
| H1674 H | 8/1997 | Ames et al. |
| 5,656,111 A | 8/1997 | Dilnik et al. |
| 5,662,637 A | 9/1997 | Kitaoka et al. |
| 5,662,638 A | 9/1997 | Johnson et al. |
| 5,665,084 A | 9/1997 | Richmond |
| 5,669,897 A | 9/1997 | Lavon et al. |
| 5,685,873 A | 11/1997 | Bruemmer |
| 5,685,874 A | 11/1997 | Buell et al. |
| 5,690,626 A | 11/1997 | Suzuki et al. |
| 5,690,627 A | 11/1997 | Clear et al. |
| 5,693,038 A | 12/1997 | Suzuki et al. |
| 5,695,488 A | 12/1997 | Sosalla |
| 5,695,868 A | 12/1997 | McCormack |
| D389,320 S | 1/1998 | Vinnage et al. |
| 5,707,364 A | 1/1998 | Coates |
| 5,711,832 A | 1/1998 | Glaug et al. |
| 5,725,518 A | 3/1998 | Coates |
| 5,759,317 A | 6/1998 | Justmann |
| 5,772,649 A | 6/1998 | Siudzinski |
| 5,772,825 A | 6/1998 | Schmitz |
| 5,788,685 A | 8/1998 | Ronnberg et al. |
| 5,788,797 A | 8/1998 | Herrin et al. |
| 5,795,433 A | 8/1998 | Niedermeyer |
| 5,827,259 A | 10/1998 | Laux et al. |
| 5,827,260 A | 10/1998 | Suzuki et al. |
| 5,830,206 A | 11/1998 | Larsson |
| 5,843,056 A | 12/1998 | Good et al. |
| 5,855,574 A | 1/1999 | Kling et al. |
| 5,876,531 A | 3/1999 | Jacobs et al. |
| 5,897,545 A | 4/1999 | Kline et al. |
| 5,899,896 A * | 5/1999 | Suprise et al. .............. 604/358 |
| 5,904,673 A | 5/1999 | Roe et al. |
| 5,904,802 A | 5/1999 | Niedermeyer |
| 5,916,203 A | 6/1999 | Brandon et al. |
| 5,916,207 A * | 6/1999 | Toyoda et al. ................. 24/442 |
| 5,919,334 A | 7/1999 | Niedermeyer |
| 5,938,652 A | 8/1999 | Sauer |
| 5,944,707 A | 8/1999 | Ronn |
| 5,961,761 A | 10/1999 | Heindel et al. |
| 5,971,153 A | 10/1999 | Bauer et al. |
| 6,022,430 A | 2/2000 | Blenke et al. |
| 6,022,431 A | 2/2000 | Blenke et al. |
| 6,022,432 A | 2/2000 | Elsberg et al. |
| 6,030,373 A * | 2/2000 | VanGompel et al. ........ 604/386 |
| 6,036,805 A | 3/2000 | McNichols |
| 6,045,543 A * | 4/2000 | Pozniak et al. ........ 604/385.01 |
| 6,113,717 A | 9/2000 | Vogt et al. |
| 6,149,638 A | 11/2000 | Vogt et al. |
| 6,287,287 B1 | 9/2001 | Elsberg |
| 6,322,552 B1 | 11/2001 | Blenke et al. |
| 6,336,922 B1 | 1/2002 | VanGompel et al. |
| 6,361,527 B1 | 3/2002 | Van Gompel et al. |

| | | |
|---|---|---|
| CA | 2096672 | 11/1993 |
| CA | 2103992 A1 | 2/1994 |
| CA | 2187021 A1 | 10/1995 |
| CA | 2187366 A1 | 10/1995 |
| EP | 0 206 208 B1 | 12/1986 |
| EP | 0 217 032 A2 | 4/1987 |
| EP | 0 251 251 A3 | 1/1988 |
| EP | 0 463 276 A1 | 1/1992 |
| EP | 0 532 034 A2 | 3/1993 |
| EP | 0 544 703 B1 | 6/1993 |
| EP | 0 696 911 B1 | 2/1996 |
| EP | 0 753 292 A2 | 1/1997 |
| EP | 0 487 758 B1 | 3/1997 |
| EP | 0 597 331 | 11/1997 |
| EP | 0 809 992 A1 | 12/1997 |
| EP | 0 878 180 A2 | 11/1998 |
| FR | 2566631 | 3/1984 |
| GB | 1 520 740 | 8/1978 |
| GB | 2 244 422 B | 12/1991 |
| GB | 2 267 024 B | 11/1993 |
| GB | 2 288 314 A | 10/1995 |
| GB | 2 288 315 A | 10/1995 |
| GB | 2 288 316 A | 10/1995 |
| GB | 2 291 783 A | 2/1996 |
| GB | 2 294 867 A | 5/1996 |
| GB | 2 297 473 A | 6/1996 |
| GB | 2 308 290 | 3/1999 |
| JP | 6-77718 U | 11/1994 |
| JP | 7-213553 A | 8/1995 |
| JP | 7-227407 A | 8/1995 |
| JP | 7-255773 A | 10/1995 |
| JP | 7-299094 A | 11/1995 |
| JP | 8-229072 A | 9/1996 |
| JP | 9-287 U | 5/1997 |
| JP | 11-47188 A | 2/1999 |
| WO | WO 83/04163 A1 | 12/1983 |
| WO | WO 90/07313 A1 | 7/1990 |
| WO | WO 91/04724 A1 | 4/1991 |
| WO | WO 91/08725 A1 | 6/1991 |
| WO | WO 92/22274 A1 | 12/1992 |
| WO | WO 93/09742 A1 | 5/1993 |
| WO | WO 94/17768 A1 | 8/1994 |
| WO | WO 95/01148 A | 1/1995 |
| WO | WO 95/02383 A1 | 1/1995 |
| WO | WO 95/13772 A1 | 5/1995 |
| WO | WO 95/22951 A1 | 8/1995 |
| WO | WO 95/27460 A1 | 10/1995 |
| WO | WO 95/27462 A1 | 10/1995 |
| WO | WO 95/29657 A1 | 11/1995 |
| WO | WO 96/03101 A1 | 2/1996 |
| WO | WO 96/18315 A1 | 6/1996 |
| WO | WO 96/29037 | 9/1996 |
| WO | WO 96/32084 A1 | 10/1996 |
| WO | WO 97/15260 A1 | 5/1997 |
| WO | WO 97/23186 A1 | 7/1997 |
| WO | WO 97/25951 A1 | 7/1997 |
| WO | WO 97/31605 A1 | 9/1997 |
| WO | WO 97/32555 A1 | 9/1997 |
| WO | WO 97/33547 A1 | 9/1997 |
| WO | WO 97/46197 A1 | 12/1997 |
| WO | WO 97/47265 | 12/1997 |
| WO | WO 97/48357 | 12/1997 |
| WO | WO 98/03140 A1 | 1/1998 |
| WO | WO 98/18421 A1 | 5/1998 |
| WO | WO 98/29251 | 7/1998 |
| WO | WO 98/51252 | 11/1998 |
| WO | WO 98/56328 A1 | 12/1998 |
| WO | WO 9853780 A1 * | 12/1998 ........... A61F 13/15 |

| WO | WO 99/07319 A1 | 2/1999 | |
| WO | WO 99/56688 | 11/1999 | |
| WO | WO 99/65438 | * 12/1999 | ........... A61F 13/15 |
| WO | WO 99/65442 | 12/1999 | |
| WO | WO 00/37010 | 6/2000 | |
| WO | WO 01/43682 A1 | 6/2001 | |
| WO | WO 01/43683 A1 | 6/2001 | |
| WO | WO 01/70155 A1 | 9/2001 | |

OTHER PUBLICATIONS

Derwent World Patent Database abstract of JP 6-063076 A: Description of Kao Corp. (Kaos), "Throw Away Diaper Or Nappy."

Derwent World Patent Database abstract of JP 95-044941 B2: Description of Zuiko KK (ZUIK-N), "Simple Solid Diaper For Eliminating Waste of Material by Using Square Shape."

Derwent World Patent Database abstract of JP 9-276334 A: Description of Kao Corp (Kaos), "Disposable Baby Nappy."

Derwent World Patent Database abstract of JP 11-070143 A: Description of TOYO EISAI KK (TOEI-N), "Disposable Diaper For Adults and Children."

Derwent World Patent Database abstract of JP 11-076299 A: Description of UNI-CHARM KK (UNIC-N), "Disposable Diaper."

* cited by examiner

PANT-LIKE DISPOSABLE ABSORBENT ARTICLES

This application is a continuation-in-part of application Ser. No. 09/216,545 entitled PANT-LIKE DISPOSABLE ABSORBENT ARTICLES WITH AN EASY OPENING FEATURE and filed in the U.S. Patent and Trademark Office on Dec. 18, 1998. The entirety of application Ser. No. 09/216,545 is hereby incorporated by reference.

FIELD OF THE INVENTION

The present invention relates to disposable absorbent articles which are adapted to contain body exudates. More particularly, the present invention relates to prefastened, refastenable, pant-like disposable absorbent articles.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the caregiver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. In such circumstances it is also desirable that the caregiver or the wearer may be able to apply the absorbent article to a wearer in a prone position similar to a conventional diaper. For example, such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper has been applied by being positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached.

Several attempts have been made to provide absorbent articles which effectively contain body exudates, are capable of being pulled up or down over the hips of the wearer and provide ease of cleaning and removal after being soiled. For example, some conventional absorbent articles, such as conventional training pants, have included integral side panels which connect the front waist portion to the back waist portion of the absorbent article. These side panels have longitudinal seams which provide full hip and lower torso coverage to provide the pant-like configuration. The side panels have also been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely, which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of both conventional training pants and conventional diapers. That is, there remains a need for absorbent articles which conform to the wearer to effectively contain bodily exudates, which are capable of being pulled up and down over the hips and buttocks of the wearer without opening, which are readily secured about and removed from the wearer in a convenient and clean manner and which allow easy inspection by the care giver to assist in determining whether the article is soiled. Moreover, there is a need that such pant-like disposable absorbent articles are capable of providing the fit and comfort of a conventional diaper.

SUMMARY OF THE INVENTION

In response to the difficulties and problems discussed above, new pant-like disposable absorbent articles have been discovered. In one aspect, the present invention concerns a pant-like, refastenable, disposable absorbent article which defines a front waist region, a back waist region, a crotch region which extends between and connects the waist regions, a longitudinal direction and a lateral direction. The absorbent article includes an absorbent chassis which defines an exterior surface, an interior surface opposite the exterior surface, a pair of laterally opposed side edges and a pair of longitudinally opposed waist edges. The absorbent article also includes a pair of opposed side panels which extend outward from and between the side edges of the absorbent chassis in the front waist region and back waist region of the absorbent article to define a waist opening and a pair of leg openings in the pant-like disposable absorbent article. Each of the opposed side panels defines a first side margin which is permanently attached to the side edge of the absorbent chassis in either the front waist region or the back waist region of the absorbent article to provide a permanent joint and a second side margin which is releasably attached to the side edge of the absorbent chassis in the other waist region of the absorbent article to provide a releasable joint. The absorbent article also includes a fastener which is permanently attached to each of the second side margins of the side panels. The fastener defines a fastener edge length in the longitudinal direction and the releasable joint defines a releasable joint length in the longitudinal direction wherein the releasable joint length is greater than the fastener edge length.

In another aspect, the present invention concerns a pant-like, refastenable, disposable absorbent article which defines a front waist region, a back waist region, a crotch region which extends between and connects the waist regions, a longitudinal direction and a lateral direction. The absorbent article includes an absorbent chassis, a pair of opposed back panels and a pair of opposed front panels. The absorbent chassis defines an exterior surface, an interior surface opposite the exterior surface, a pair of laterally opposed side edges and a pair of longitudinally opposed waist edges. The opposed back panels are permanently attached to the side edge of the absorbent chassis in the back waist region of the absorbent article. The opposed front panels are releasably attached to the side edge of the absorbent chassis in the front waist region of the absorbent article to provide a releasable joint. The front panel and back panel on each side edge of the absorbent chassis extend laterally outward from the absorbent chassis and are connected together along a side seam to define a waist opening and a pair of leg openings and provide the pant-like, refastenable, disposable absorbent article. The absorbent article also includes a fastener which is permanently attached to each of the front panels adjacent the releasable joint. The fastener defines a fastener edge length in the longitudinal direction and the releasable joint defines a releasable joint length in the longitudinal direction wherein the releasable joint length is greater than the fastener edge length.

In yet another aspect, the present invention concerns a pant-like, refastenable, disposable absorbent article which defines a front waist region, a back waist region, a crotch region which extends between and connects the waist regions, a longitudinal direction and a lateral direction. The absorbent article includes an absorbent chassis, a pair of opposed back panels and a pair of opposed front panels. The absorbent chassis defines an exterior surface, an interior surface opposite the exterior surface, a pair of laterally opposed side edges and a pair of longitudinally opposed waist edges. The opposed back panels are permanently attached to the side edge of the absorbent chassis in the back waist region of the absorbent article. The opposed front panels are permanently attached to the side edge of the absorbent chassis in the front waist region of the absorbent article. The absorbent article also includes a releasable side seam wherein the front panel and the back panel on each side of the absorbent chassis are releasably connected together to define a releasable joint and a waist opening and a pair of leg openings to provide the pant-like refastenable, disposable absorbent article. The absorbent article also includes a fastener permanently attached to each of the back panels adjacent the releasable side seams. The fastener defines a fastener edge length in the longitudinal direction and the releasable joint defines a releasable joint length in the longitudinal direction wherein the releasable joint length is greater than the fastener edge length.

The present invention advantageously provides pant-like, refastenable disposable absorbent articles which include a releasable joint and a fastener which is configured to be smaller in the longitudinal direction than the releasable joint. As such, the proportional longitudinal length of the fastener better accommodates the hips and legs of the wearer and thereby provides improved fit and comfort in use when used in a conventional diaper configuration. In particular, the present invention provides pant-like disposable absorbent articles which are capable of being reliably pulled up or down over the hips of the wearer to assist in the toilet training of the wearer similar to conventional training pants. Moreover, similar to conventional diapers, the pant-like disposable absorbent articles of the present invention can advantageously be applied to and removed from the wearer similar to conventional diapers after they have been soiled with relative ease and cleanliness. Further, the pant-like disposable absorbent articles of the present invention allow easy inspection by the caregiver to assist in determining whether the article is soiled similar to conventional diapers. Still further, the pant like disposable absorbent articles provide the combination of a side seam and smaller, proportional fasteners. Such a combination provides the security and hip coverage when the article is used in the pant-like configuration as well as greater flexibility and range of motion when used in a conventional diaper configuration.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns pant-like, refastenable, disposable absorbent articles which are adapted to be worn adjacent to the body of a wearer to absorb and contain various exudates discharged from the body and methods of making the same. The pant-like absorbent articles are configured to closely conform to the body of the wearer to effectively contain body exudates while being capable of being pulled up or down over the hips and buttocks of the wearer. The absorbent articles also include a pair of releasable joints and a pair of refastenable fasteners such that the absorbent article can be secured to and removed directly from the waist of the wearer and easily inspected to determine if they have been soiled during use. Moreover, the refastenable fasteners are smaller in the longitudinal direction than the releasable joints to provide increased flexibility and a greater range of motion when used in a conventional diaper configuration. Such a configuration can lead to less irritation and red marking. As such, the pant-like, refastenable, disposable absorbent articles of the present invention can function in a similar manner to conventional training pants when left in the prefastened, pant-like configuration or they can be unfastened prior to or during use to function in a refastenable manner similar to conventional diapers. As used herein, the term "disposable" refers to articles which are intended to be discarded after a limited use and which are not intended to be laundered or otherwise restored for reuse.

The pant-like disposable absorbent articles of the present invention will be described in terms of a disposable, pant-like diaper article which is adapted to be worn by infants about the lower torso. In particular, the pant-like disposable absorbent articles will be described in terms of a pant-like, refastenable, disposable diaper having prefastened side panels, and a pair of releasable joints and refastenable fasteners. It is understood that the articles and methods of the present invention are equally adaptable for other types of absorbent articles such as adult incontinent products, training pants, feminine hygiene products, other personal care or health care garments, and the like.

Figure 1:
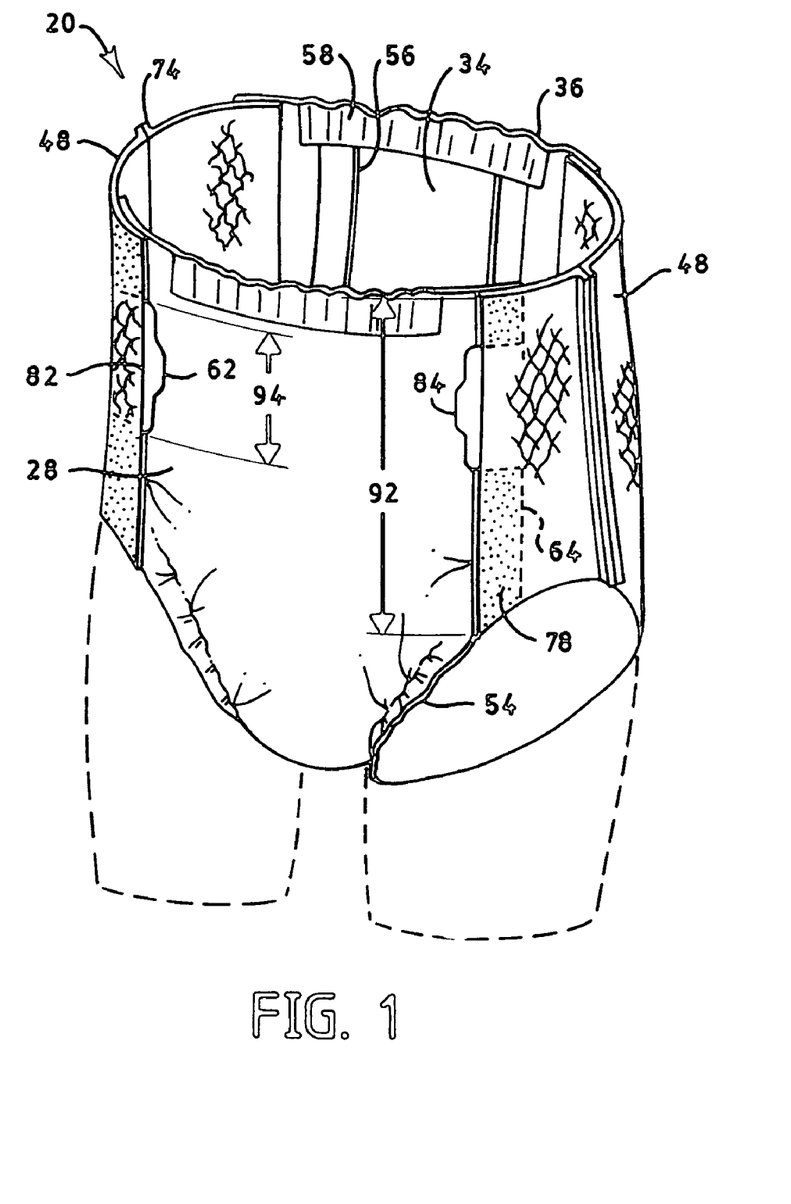
FIG. 1 representatively shows a perspective view of an example of a pant-like, refastenable disposable absorbent article of the present invention.
Figure 2:
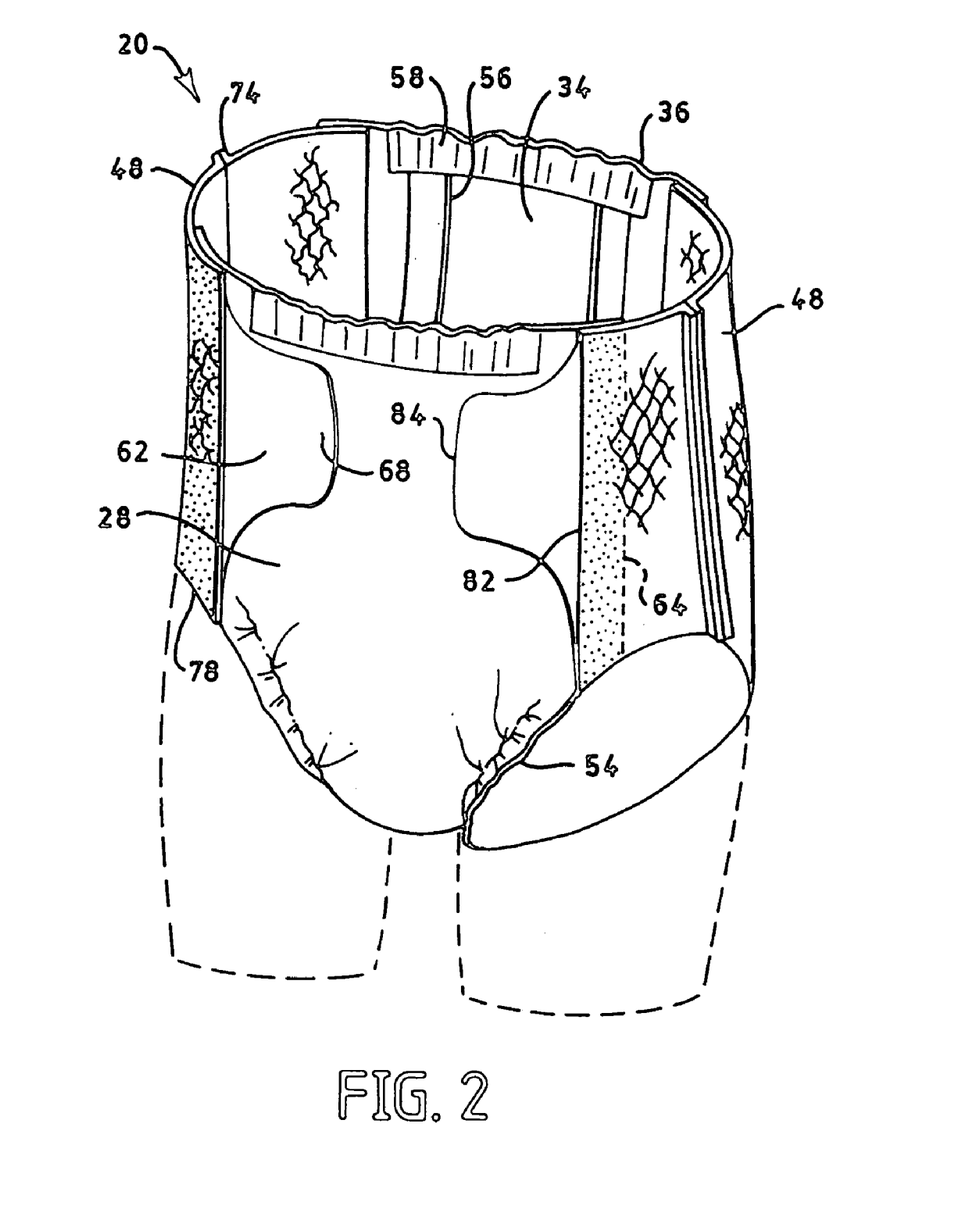
FIG. 2 representatively shows a perspective view of an example of an alternate embodiment of a pant-like, refastenable disposable absorbent article of the present invention.
Figure 3:
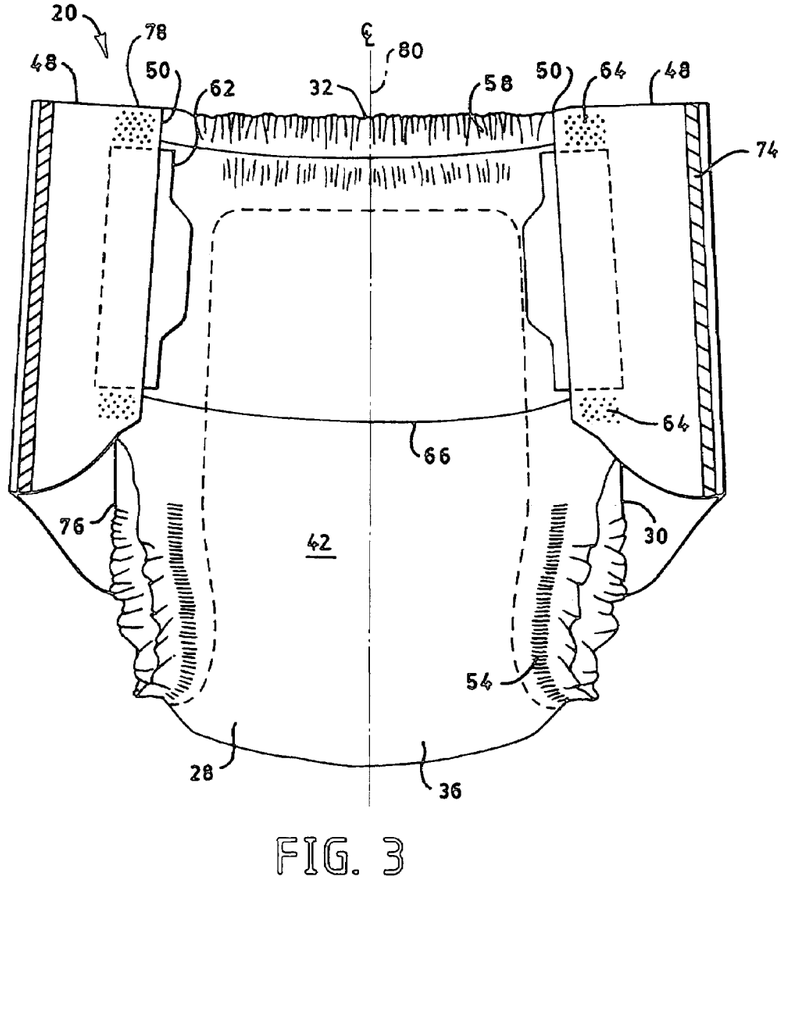
FIG. 3 representatively shows a front plan view of the pant-like, refastenable disposable absorbent article of FIG. 1.
Figure 4:
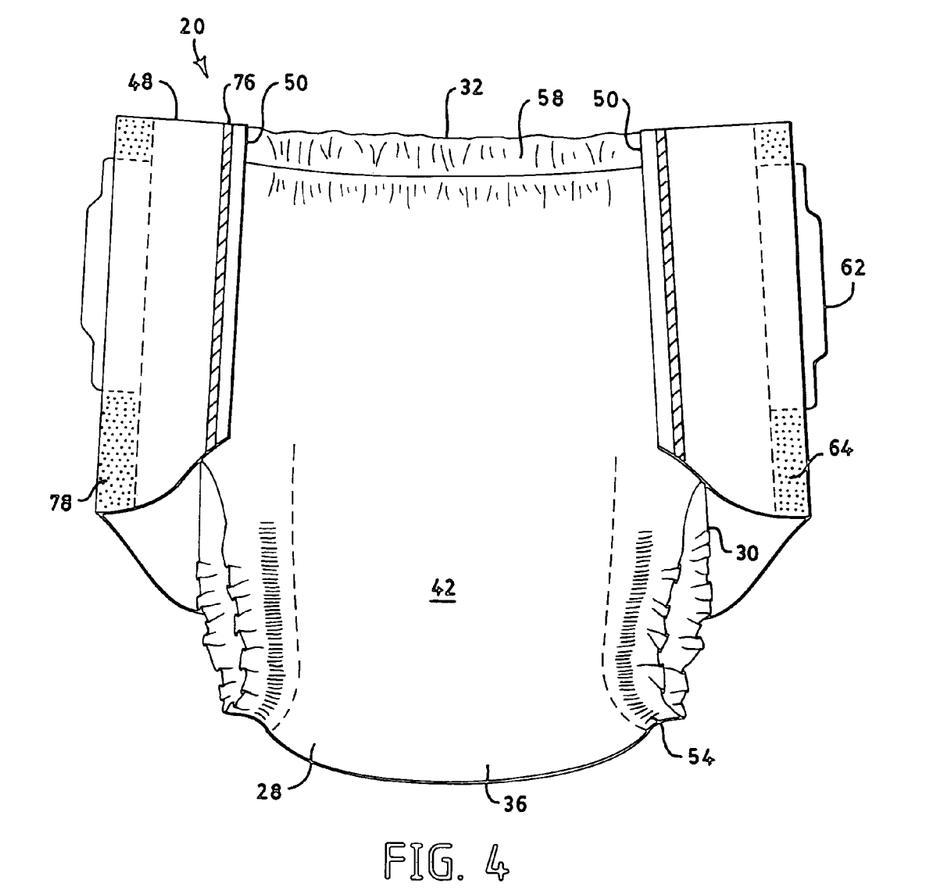
FIG. 4 representatively shows a front plan view of an example of a pant like, refastenable disposable absorbent article wherein the refastenable joint and the fasteners are located in the side seams.
Figure 5:
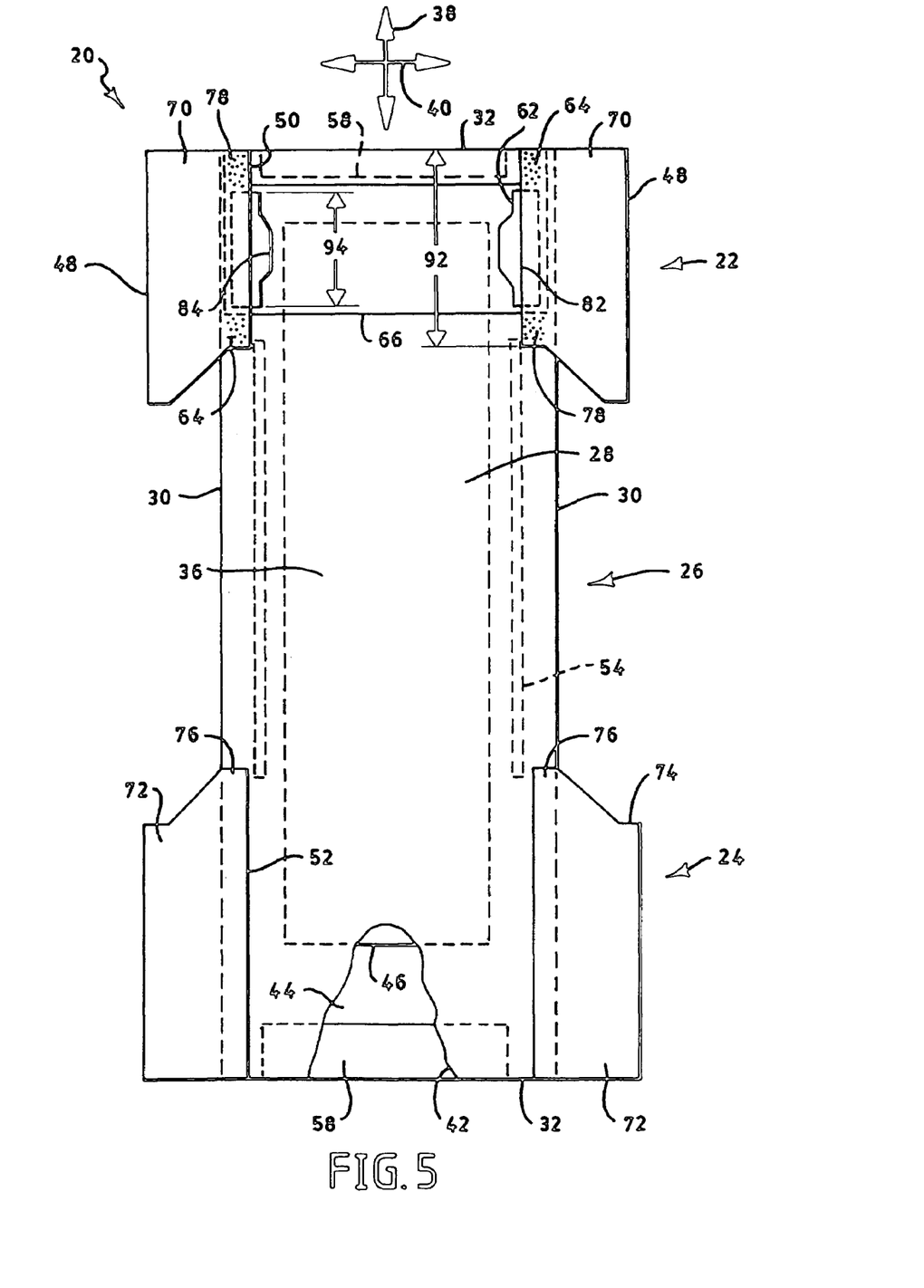
FIG. 5 representatively shows a plan view of the disposable absorbent article of FIG. 1 with the permanent joints broken, and in a stretched and laid flat condition with the surface of the article which contacts the wearer's clothing facing the viewer and with portions of the article partially cut away to show the underlying features.

FIG. 1 representatively illustrates an example of a pant-like, refastenable disposable diaper, as generally indicated at 20, of the present invention. FIG. 2 representatively illustrates an alternative embodiment of the pant-like, refastenable, disposable diaper 20 of the present invention. FIG. 3 representatively illustrates a front plan view of the prefastened diaper of FIG. 1. FIG. 4 representatively illustrates a front plan view of an alternative embodiment of the disposable diaper of the present invention wherein the releasable joints and the fasteners are located at the side seams. FIG. 5 representatively illustrates the prefastened diaper of FIG. 1 with the permanent joints 76 opened, and in a stretched and laid flat configuration with the surface of the diaper adapted to contact the wearer's clothing facing the viewer and with portions of the diaper partially cut away to show the underlying features. As illustrated in FIG. 5, the diaper 20 defines a front waist region 22, a back waist region 24, a crotch region 26 which extends between and connects the front and back waist regions 22 and 24, a longitudinal direction 38 and a lateral direction 40.

The illustrated diaper 20 includes an absorbent chassis 28 and a pair of laterally opposed side panels 48. The absorbent chassis 28 defines a pair of laterally opposed side edges 30, a pair of longitudinally opposed waist edges 32, an interior surface 34 which is configured to contact the wearer, and an exterior surface 36 opposite the interior surface 34 which is configured to contact the wearer's clothing in use. The absorbent chassis 28, as representatively illustrated in FIG. 5, includes an outer cover 42, a bodyside liner 44 which is connected to the outer cover 42 in a superposed relation, and an absorbent core 46 which is located between the outer cover 42 and the bodyside liner 44. The side panels 48 extend laterally outward from and between each opposed side edge 30 of the absorbent chassis 28 of the front and back waist regions 22 and 24.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The side panels 48 comprise the portions of the diaper which, when worn, are positioned on the side hip regions of the wearer. The laterally opposed side edges 30 of the absorbent chassis 28 and the side panels 48 of the diaper 20 generally define leg openings which may be curvilinear. The waist edges 32 of the absorbent chassis of the diaper 20 and the side panels 48 are configured to encircle the waist of the wearer when worn and provide a waist opening when fastened which defines a waist perimeter dimension.

The illustrated diaper 20 further includes a pair of fasteners 62 and a pair of releasable joints 78. The releasable joints 78 releasably secure each of the side panels 48 of the diaper 20 with the opposed side edges 30 of the absorbent chassis 28 to provide the pant-like prefastened absorbent article. A fastener 62 located adjacent each of the releasable joints 78 may be used to refastenably engage the back waist region 24 to the front waist region 22 when the releasable joints 78 are broken. The releasable joints 78 may be comprised of the fasteners 62 or releasable bonds 64 or suitable combinations thereof. The diaper 20 may further include an attachment panel 66 located on the exterior surface of the absorbent chassis 28 to which the fasteners 62 are configured to releasably engage.

The absorbent chassis 28 is configured to contain and/or absorb any body exudates discharged from the wearer. Whereas, the side panels 48 and the combination of the releasable joints 78 and/or the refastenable fasteners 62 are configured to maintain the diaper 20 about the waist of the wearer and provide a pant-like appearance. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 may be of various suitable shapes. For example, in the unfastened configuration as illustrated in FIG. 5, the diaper may have an overall rectangular shape, T-shape or an approximately hour-glass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 46 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 54 and 58 and the fasteners 62, may be assembled into the diaper 20 article by employing the above-identified attachment mechanisms. Desirably, the majority of the diaper components are assembled together using ultrasonic bonding techniques for reduced manufacturing cost.

The outer cover 42 of the absorbent chassis 28 of the diaper 20, as representatively illustrated in FIG. 5, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material.

For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 46. Still further, the outer cover 42 may optionally be composed of a micro-porous "breathable" material which permits vapors to escape from the absorbent core 46 while still preventing liquid exudates from passing through the outer cover 42. The outer cover 42 can also be embossed or otherwise provided with a matte finish to provide a more aesthetically pleasing appearance.

The bodyside liner 44, as representatively illustrated in FIG. 5, suitably presents a bodyfacing surface which is compliant, soft feeling, and nonirritating to the wearer's skin. Further, the bodyside liner 44 may be less hydrophilic than the absorbent core 46, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 46.

Various woven and nonwoven fabrics can be used for the bodyside liner 44. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto to which is configured to treat or be transferred to the wearer's skin.

The absorbent core 46 of the diaper 20, as representatively illustrated in FIG. 5, may suitably comprise a matrix of hydrophilic fibers, such as a web of cellulosic fluff, mixed with particles of a high-absorbency material commonly known as superabsorbent material. In a particular embodiment, the absorbent core 46 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 46 to better contain and absorb body exudates. The concentration of the superabsorbent particles may also vary through the thickness of the absorbent core 46. Alternatively, the absorbent core 46 may comprise a laminate of fibrous webs and superabsorbent material or other suitable means of maintaining a superabsorbent material in a localized area.

The absorbent core 46 may have any of a number of shapes. For example, the absorbent core may be rectangular, I-shaped, or T-shaped. It is generally preferred that the absorbent core 46 be narrow in the crotch area of the diaper 20. It has been found that the absorbent chassis 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent chassis 28 allows the absorbent chassis 28 to better fit between the legs of the wearer. The size and the absorbent capacity of the absorbent core 46 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent core 46.

Optionally, a substantially hydrophilic tissue wrapsheet (not illustrated) may be employed to help maintain the integrity of the airlaid fibrous structure of the absorbent core 46. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent core 46.

As representatively illustrated in FIG. 1, the absorbent chassis 28 of the disposable diaper 20 may include a pair of containment flaps 56 which are configured to provide a barrier to the lateral flow of body exudates. The containment flaps 56 may be located along the laterally opposed side edges 30 of the absorbent chassis 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent chassis 28 or may only extend partially along the length of the absorbent chassis 28. When the containment flaps 56 are shorter in length than the absorbent chassis 28, the containment flaps 56 can be selectively positioned anywhere along the side edges 30 of the absorbent chassis 28. In a particular aspect of the invention, the containment flaps 56 extend along the entire length of the absorbent chassis 28 to better contain the body exudates.

Such containment flaps 56 are generally well known to those skilled in the art. For example, suitable constructions and arrangements for containment flaps 56 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the absorbent chassis 28 of the diaper 20 to further prevent leakage of body exudates and support the absorbent chassis 28. For example, as representatively illustrated in FIGS. 1–3, the diaper 20 of the present invention may include a pair of leg elastic members 54 which are connected to the laterally opposed side edges 30 of the absorbent chassis 28 in the crotch region 26 of the diaper 20 and a pair of waist elastic members 58 which are connected to the longitudinally opposed waist edges 32 of the absorbent chassis 28 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

As representatively illustrated in FIGS. 1–3, the diaper 20 further includes a pair of laterally opposed side panels 48. Each side panel 48 defines a first side margin 50 which is joined to the side edge 30 of the absorbent chassis 28 in the front waist region 22 and a second side margin 52 which is joined to the side edge 30 of the absorbent chassis 28 in the back waist region 24. The illustrated side panels 48 are permanently connected to the side edges 30 of the absorbent chassis 28 in at least one of the waist regions 22 and 24 and may be releasably attached to the side edges 30 of the absorbent chassis 28 in the opposite waist region.

For example, as representatively illustrated in FIGS. 1–5, the second side margins 52 of the side panels 48 of the diaper 20 may be permanently secured to and extend laterally beyond the side edges 30 of the diaper 20 in the back waist region 24 of the diaper 20 to provide a permanent joint 76. The side panels 48 are permanently connected to the diaper 20 along permanent joint 76 using attachment means known to those skilled in the art such as adhesive, thermal or ultrasonic bonding. As discussed above, the side panels 48 are desirably permanently connected to the absorbent chassis 28 of the diaper 20 using ultrasonic bonding for improved manufacturing efficiency and reduced raw material cost. In such a configuration, the first side margin 50 of each of the side panels 48 may be releasably attached to the side edges 30 of the absorbent chassis 28 in the front waist region 22 of the diaper 20 to provide a releasable joint 78. The releasable joint 78, in such a configuration, is located on the front abdominal region of the wearer for easy access to the care giver.

Alternatively, the side margins of the side panels 48 may be permanently connected to the side edges 30 of the absorbent chassis 28 in the front waist region 22 and releasably attached to the side edges 30 of the absorbent chassis 28 in the back waist region 24 of the diaper 20 if it is desired that the fasteners be located towards the back of the wearer. Such a configuration may be desirable to prevent a wearer from unfastening the article prematurely. Still further, as discussed in more detail below, the side margins 50 and 52 of the side panels 48 may be permanently connected to the side edges 30 of the absorbent chassis 28 in both the front and back waist regions 22 and 24. For such a configuration, the side panels 48 may include at least two individual panels that are releasably connected together along a side seam 74 to provide the releasable joints 78.

In yet another alternative, the side panels 48 may be provided by a portion of the absorbent chassis 28 (not illustrated). For example, the side panels 48 may be provided by the outer cover 42, the bodyside liner 44 or a combination of the two. If the outer cover 42 provides the side panels 48, the outer cover 42 in the front or back waist region 22 and 24 may extend beyond the side edges 30 of the absorbent chassis 28 in the lateral direction 40 and be releasably attached to the front or back waist region 22 and 24 of the diaper 20. Accordingly, the releasable attachment of the portion of the outer cover 42 providing the side panels 48 to the front or back waist regions 22 and 24 of the diaper 20, provides the releasable joints 78.

The releasable joints 78 of the present invention are defined by the releasably attached portion of the joint which comprises the releasable joint 78. That is, the releasable joint 78 is comprised of the entire intact seam, which may or may not extend from the waist opening to the leg opening of the diaper 20. Prior to opening the releasable joint 78, the intact portion of the releasable joint 78 may be a continuous intact seam, a discontinuous seam, or alternatively a partially intact seam. Accordingly, the releasable joint 78 extends in the longitudinal direction 38 from the initial intact portion of the joint below the waist opening to the final intact portion of the joint above the leg opening, regardless of any gaps which may exist within the intact yet releasable portion of the releasable joint 78. Therefore, the length of the releasable joint 78 may not necessarily equal the entire length of the seam from the leg opening to the waist opening, but does equal the length of the intact portion of the releasable joint 78 including any gaps which may exist therein.

For example, as representatively illustrated in FIGS. 1 and 5, the releasable joints 78 may be provided by the fastener 62 and releasable bonds 64 as is discussed in greater detail below. As such, gaps may exist between the releasable bonds 64 and the fastener 62. Moreover, the releasable bonds 64 may also be configured to include gaps and/or interruptions located between individual bonds. Accordingly, as described above, the releasable joints 78 include all of the intact portions provided by the fasteners 62 and the releasable bonds 64 and any gaps or interruptions which may exist therein.

The releasable joints 78 may be provided by conventional fasteners including the refastenable fasteners 62 and/or any type of bonding such as adhesive, thermal, cohesive, and ultrasonic bonding as are well known to those skilled in the art. For example the releasable joint may include releasable bonds 64 for improved reliability of maintaining the article in the prefastened condition particularly when it is being pulled on or off over the hips of the wearer. Absorbent articles including such releasable bonds and methods of making such are further described in U.S. patent application entitled "DISPOSABLE ABSORBENT ARTICLES HAVING PASSIVE SIDE BONDS AND ADJUSTABLE FASTENING SYSTEMS" filed in the name of Elsberg on Jun. 19, 1998 and assigned U.S. Ser. No. 09/100,574, and U.S. Pat. No. 6,036,805 entitled "METHOD OF MAKING AN ABSORBENT ARTICLE WITH PREFASTENED SIDE PANELS AND ABSORBENT ARTICLES MADE BY THE SAME" issued Mar. 14, 2000 Jun. 19, 1998 to McNichols, the disclosures of which are hereby incorporated by reference.

For example, as representatively illustrated in FIGS. 1–3, and 5, the pant-like diaper 20 may includes releasable bonds 64 which releasably connect the side panels 48 to the front waist region 22 of the diaper 20. In such a configuration, the releasable bonds 64 provide the releasable joints 78 and assist the fasteners 62 in maintaining the diaper 20 in a prefastened condition as the diaper 20 is pulled up or down over the hips of the wearer. Moreover, when the releasable bonds 64 provide the releasable joints 78 and the fasteners 62 are engaged, they assist the fasteners 62 in preventing movement and shifting of the waist regions 22 and 24 and side panels 48 relative to each other for improved fit and performance. The releasable bonds 64 also provide improved hip coverage and prevent rollover or folding of the side edges 30 and waist edges 32 of the absorbent chassis 28 of the prefastened diaper 20 as it is pulled over the wearers hips. Such prevention of rollovers and foldovers can reduce the level of contact between the fasteners 62 and the skin of the wearer which can desirably result in reduced skin irritation and redness.

The releasable bonds 64 may be discrete point bonds, dashed lines, continuous lines, discontinuous lines and the like, or combinations thereof. Moreover, the releasable bonds 64 may have any shape such as circular, square, triangular and the like. Desirably, the releasable bonds 64 are ultrasonic point bonds for improved manufacturing efficiency. In such a configuration, the ultrasonic bonds will be destroyed upon the first disengagement of the releasable joints 78.

The diaper 20 is provided in a pant-like configuration with the releasable joints 78 intact. In such a configuration, the diaper 20 may be pulled on or off over the legs and hips of the wearer. Further, the releasable joints 78 should have a relatively low peel strength such that the joint can be broken by the caregiver if desired without tearing or severely damaging the other portions of the diaper 20. As such, the releasable joints 78 may be disengaged to inspect the diaper for possible soiling. If the diaper 20 is soiled during use, the releasable joints 78 may be disengaged to easily remove the diaper 20 from the waist of the wearer with reduced risk of undesirably soiling the clothes or legs of the wearer. Finally, the releasable joints 78 may also be disengaged to allow the user the option of applying the pant-like diaper 20 in a conventional diaper configuration.

Each of the side panels 48 may include one or more individual, distinct pieces of material. For example, in the illustrated embodiments, each side panel 48 includes a front side panel 70 and a back side panel 72. The front side panel 70 includes the first side margin 50 which may be releasably attached to the side edges 30 of the absorbent chassis 28 in the front waist region 22 of the diaper 20 to provide the releasable joint 78. The back side panel 72 includes the second side margin 52 which may be permanently connected to the side edges 30 of the absorbent chassis 28 in the back waist region 24 of the diaper 20 to provide the permanent joint 76. In such a configuration, the laterally outward edge of the front side panel 70 is connected to the laterally outward edge of each back side panel 72 to provide a side seam 74 as illustrated in FIGS. 1–4. Desirably, the laterally outward edges of the front and back side panels 70 and 72 are attached to each other along the side seam 74 using ultrasonic bonding for improved manufacturing efficiency and reduced raw material cost. Side panels 48 having such front and back side panels 70 and 72 provide improved manufacturability. In an alternative configuration, each side panel 48 may include a single piece of material which is folded over upon itself during manufacturing along a fold line located in a similar location to the side seam 74.

The side seams 74 of the present invention may be arranged in a number of configurations. For example, as representatively illustrated in FIGS. 1–4, the side seams 74 may be provided in a flange bonded configuration. In the illustrated embodiments the interior surface of the front panel 70 is attached to the interior surface of the back panel 72 in an overlapping configuration to provide the flanged side seams 70. Alternatively, the side seams 74 may be provided in a lap bonded configuration (not illustrated). As such, the exterior surface 36 of one of the front or back panels 70 and 72 are bonded to the interior surface 34 of the opposing front or back panel 70 and 72 in an overlapping arrangement. Such a configuration may be desirable when the side seams 74 provide the releasable joints 78, as a lap bonded configuration would subject the side seams 74 primarily to shear forces during use, thereby providing enhanced seam strength.

As representatively illustrated in FIG. 4, the side seams 74 may provide the releasable joint 78. In such a configuration, the first side margins 50 of the front side panels 70 are permanently attached to the side edges 30 of the absorbent chassis 28 in the front waist region 22. Likewise, the second side margins 52 of the back side panels 72 are permanently attached to the side edges 30 of the absorbent chassis 28 in the back waist region 24. The releasable joint 78 is created by the releasable attachment of the laterally outward edges of the front side panel 70 and the back side panel 72 at the side seam 74. Materials suitable for the side panels 48 of the diaper 20 are generally known to those skilled in the art. For example, suitable materials for the side panels 48 include those materials described above as being suitable for the outer cover 42 or bodyside liner 44 of the absorbent chassis 28 of the diaper 20 such as woven and nonwoven materials or laminates of such materials. Desirably, the side panels 48 are extensible or elastic to provide improved fit about the wearer. For example, the side panels 48 may comprise a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. When made with extensible or elastic materials, the side panels 48 are desirably capable of elongating in the lateral direction 40 from about 10 to about 400 percent, more desirably at least about 100 percent, even more desirably from about 100 to about 300 percent, and still yet more desirably from about 150 to about 250 percent for improved fit and performance. The stretchability of the side panels when elastic materials are used, allows the side panels 48 to stretch over and around the hips of the wearer as the prefastened diaper is pulled on while still maintaining proper fit at the waist after the diaper is correctly positioned on the wearer.

Desirably, the side panels 48 are a neck-bonded laminate material for improved manufacturing due to its ability to stretch in the cross machine direction. For example, in a particular embodiment, the side panels 48 include a neck-bonded laminate material which includes a urethane film having a basis weight of about 15 grams per square meter and commercially available from Shawmut Mills, a business having offices in West Bridgewater Mass., under the trade designation SHAWMUT TX-1560 sandwiched between two layers of necked, stretched spunbond. Each spunbond layer has a basis weight of about 16 grams per square meter and is composed of 3.0 denier polypropylene fibers. The composite is laminated together with an adhesive spray at an add-on rate of about 0.3 grams per square meter. A suitable adhesive is available from Findley Adhesive under the trade designation FINDLEY 2525A. Such a neck-bonded laminate material is generally capable of elongating in the cross machine direction about 185 percent.

The pant-like disposable diaper 20 of the different aspects of the present invention further includes a pair of fasteners 62 located adjacent the releasable joints 78. The fasteners 62 are configured to releasably engage one of the side panels 48 of the diaper 20 to one of the waist regions 22 or 24 of the diaper 20 to maintain the diaper about the waist of the wearer. The use of fasteners which are refastenable allows for ease of securing and removing the diaper 20 from the waist of the wearer without undesirably soiling the wearer. The use of refastenable fasteners further readily allows for the inspection of the inside of the diaper 20 to determine if it has been soiled with the ability to refasten if it is not soiled. When the fasteners 62 and/or the releasable joints 78, are engaged, the side edges 30 of the absorbent chassis 28 and edges of the side panels 48 define leg openings which are configured to encircle the legs of the wearer and the waist edges 32 of the absorbent chassis 28 and the edges of the side panels 48 opposite those defining the leg openings define a waist opening which is configured to encircle the waist of the wearer.

The fasteners 62 may be comprised of a single piece of material or a plurality of pieces. Moreover, a portion of the diaper 20 such as a portion of the side panels 48 may provide the fastener 62. The fastener 62 may be fashioned in various shapes and sizes as are known to those skilled in the art. For example, as representatively illustrated in FIGS. 1, and 3–5, the fastener 62 may be generally rectangular in shape. Alternatively, the fastener 62 may have other shapes well known to those skilled in the art. For example, as representatively illustrated in FIG. 2, the fastener may include a fastener ear 68 which extends laterally toward the longitudinal centerline 80 of the diaper 20, and to which a refastenable fastener material is attached.

In such a configuration, the fastener 62 and or a fastener ear 68 may be configured to be extensible or elastic in the lateral direction 40. As such, the fastener would provide improved fit and comfort to the wearer by allowing the fastener 62 more flexibility and range in engaging the exterior surface 36 of the diaper 20 when the diaper is being applied in a conventional configuration. For example, the fastener 62 and/or fastener ear 68 may be composed of material well known in the art. The materials may include a stretch-bonded-laminate (SBL) material, a neck-bonded-laminate (NBL) material, an elastomeric film, an elastomeric foam material, or the like such as described above as being suitable for the side panels 48.

The fasteners 62 include a refastenable fastener material that defines a distal edge 84 that is located laterally closest to the longitudinal centerline of the diaper 20. The length of the fastener in the longitudinal direction along the distal edge 84 of the fasteners 62 is smaller than the length of the releasable joint 78 in the longitudinal direction 38. For example, as representatively illustrated in FIGS. 1 and 5 the releasable joint 78 may define a releasable joint length 92 in the longitudinal direction 38 that is greater than the fastener edge length 94. In such a configuration the releasable joint length 92 is sufficient to effectively provide the diaper in a training pant configuration that has the necessary coverage and reliability. Whereas, when the releasable joint 78 is opened and diaper 20 is subsequently refastened via the refastenable fasteners 62, the fasteners 62 are sized to be relatively smaller in the longitudinal direction 38 than the refastenable joints 78. As such, the likelihood of redmarking and discomfort to the wearer, which may occur if the fastener 62 is provided as large or nearly as large in the longitudinal direction 38 as the refastenable joint 78, is desirably reduced. However, the fastener edge length 94 still advantageously provides a fastener which is sized to provide effective diaper fastening. Moreover, the relatively shorter length of the distal edge 84 of the fastener 94 allows the hips and legs of the wearer a fuller range of motion thereby further enhancing the fit and comfort of the diaper on the wearer.

In a particular embodiment, the length 92 of the releasable joint 78 in the longitudinal direction 38 may be at least about one and one half times as long as the distal edge 84 of the fastener 94, and desirably at least about twice as long, and still more desirably, three times as long as the distal edge 84 of the fastener 94. For example, if the length 94 of the distal edge 84 of the fastener 62 in the longitudinal direction was approximately 1.5 inches, then the length 92 of the releasable joint 78 may be at least about 2.25 inches and desirably at least about 3 inches, and still more desirably at least about 4.5 inches. Desirably, to provide effective fastening, the length of the fastener 62 in the longitudinal direction 38 may be from about 0.75 inches to about 3 inches.

Obtaining the proportional length 92 of the releasable joint 78 relative to the length 94 of the fastener 62 may be accomplished as is well known to those skilled in the art. For example, as representatively illustrated in FIG. 5, the fasteners 62 may have a curvilinear shape which is tapered from the inboard edge 82 of the fastener 62 to the distal edge 84 of the fastener 62 to desirably accommodate the legs of the wearer. The length of inboard edge 82 of the fastener 62 in the longitudinal direction 38 may generally correspond to the length of the releasable joint length 92. As such, the illustrated tapered fasteners 62 desirably provide the hips and legs of the wearer with a full range of motion, thereby enhancing the fit and comfort of the wearer, as described above. Moreover, since such a configuration may allow for the inboard edge 82 of the fastener 62 to be generally equal in length in the longitudinal direction 38 to the length 92 of the releasable joint 78, the fastener 62 may, upon use, effectively provide the secure fit and hip coverage of a conventional training pant without excessively reducing the flexibility and range of motion of the wearer. Alternatively, the fasteners 62 may be tapered from the inboard edge 82 to the distal edge 84 in other suitable manners such as a linear taper, a stepped taper, or the like.

As described above, the fasteners 62 may further include a stretchable or non-stretchable fastener ear 68 with the fastener 62 thereon. As representatively illustrated in FIG. 2, the fastener 62 is located at the distal edge 84 of the fastener ear 68 which is provided by the curvilinear taper of the fastener 62 and provides the smaller fastener length 94 relative to the releasable joint length 92. Alternatively, the fastener ear 68 may be generally rectangular in shape and extend in the lateral direction 40 toward the longitudinal centerline 80 of the diaper 20 in a linear fashion, maintaining the same smaller fastener length 94 over its entire lateral length. Accordingly, the fastener 62 is similarly located at the distal edge 84 of the fastener ear 68. Similar to the fastener 62, the fastener ear 68 may be provided in various shapes as are known to those skilled in the art including stepped, tapered, curvilinear, rectangular, or combinations thereof.

The fasteners 62 of the present invention are provided in combination with the releasable joints 78. As such, upon disengagement of the releasable joints 78, the fasteners 62 in the illustrated embodiments are configured to be used in conjunction with the side panels 48 to refastenably engage the back waist region 24 of the diaper 20 to the front waist region 22 of the diaper 20. When the side panels 48 are extensible or elastic, this arrangement advantageously provides the caregiver or the wearer with the added stretch from the side panels 48 while refastenably attaching the fasteners 62 to the front waist 22 region of the diaper 20. Therefore, the wearer is provided with a closer and more conforming fit, thereby reducing the possibility of leakage.

Alternatively, the releasable joint 78 and the fastener 62 may be located in the back waist region 24 of the diaper 20. In such a configuration, the fasteners 62 would engage the side panels 48 to the back waist region 24 to provide the diaper 20. This configuration may be advantageous when it is desired that the releasable joint 78 and the fasteners 62 be located towards the back of the wearer to prevent a wearer from unfastening the article or the fasteners 62 prematurely.

In yet another alternative, wherein the releasable joint 78 is provided by the side seam 74, the fasteners 62 may be configured to refastenably engage the front side panel 70 to the back waist region 24 or the back side panel 72 to the front waist region 22 to provide the diaper 20. Upon the disengagement of the releasable joints 78 and use of the fasteners 62, the wearer is provided with added comfort and flexibility at the joint of the leg and the torso as the fasteners 62 are not be as long in the longitudinal direction as the side seams 74 of the diaper 20.

The fasteners 62 may be provided in combination with the releasable joint 78 in any configuration known to those skilled in the art. For example, the fasteners 62 may be permanently attached to the diaper 20 adjacent the releasable joint 78 on the exterior surface 36 of the diaper 20. This arrangement provides the advantage of ease of manufacturability and ready accessibility of the fastener to the caregiver or wearer for use. Alternatively the fasteners 62 may be permanently attached to the diaper 20 adjacent the releasable joint 78 on the interior surface 34 of the diaper 20. Such a configuration may be desirable to prevent a wearer from easily accessing the fasteners 62 and providing a neat diaper appearance.

In the different aspects of the present invention, the fasteners 62 may be refastenably engaged with the exterior surface of the opposite waist region 22 and 24 of the diaper 20 before the diaper 20 is placed on the wearer to assist the releasable joints 78 in providing a prefastened, refastenable, pant-like disposable diaper. In such a configuration, the pant-like, refastenable diaper 20 can be pulled on or off over the legs and hips of the wearer. If the pant-like diaper 20 becomes soiled during use, the releasable joints 78 and the fasteners 62 can be disengaged to easily remove the diaper 20 from the waist of the wearer with reduced risk of undesirably soiling the clothes or legs of the wearer. The releasable joints 78 and the fasteners 62 can also be easily disengaged to inspect the diaper 20 for possible soiling or to first apply the product to the wearer if desired. Thus, the diaper 20 is configured to be pulled on or off over the hips of the wearer such as conventional training pants and can be readily applied or removed by disengaging the fasteners similar to conventional diaper articles. Moreover, the fasteners 62 can be repositioned if necessary after the prefastened diaper 20 has been pulled on over the legs and hips of the wearer to adjust the fit of the diaper to the wearer. Alternatively, the diaper 20 may be provided with the fasteners 62 in an unfastened state allowing the releasable joints 78 to provide the pant-like configuration. As such, the wearer or the care giver need only open the releasable joints 78 to apply the diaper 20 in the conventional diaper configuration.

Desirably, the fasteners 62 may be configured to refastenably engage directly with the exterior surface of the outer cover 42 of the diaper 20 to provide improved fit and ease of fastening. Alternatively, an attachment panel 66 may be located on the outer cover 42 to which the fasteners are configured to refastenably engage. As representatively illustrated in FIGS. 3 and 5, the disposable diaper 20 of the present invention may include an attachment panel 66 located on the outer cover 42 in one of the waist regions 22 and 24 on the exterior surface 36 of the absorbent chassis 28. In such a configuration, the fasteners 62 are configured to refastenably engage the attachment panel 66 to maintain the diaper 20 about the waist of the wearer after the releasable joints are broken and the fasteners are used. The attachment panel 66 may include two separate panels located along the opposed side edges 30 of the diaper 20 in one of the waist regions 22 and 24 of the diaper 20. Alternatively, the attachment panel 66 may include a single piece of material that extends substantially across the respective waist region of the diaper 20.

Suitable fasteners are well known to those skilled in the art and can include adhesive tape tab fasteners, hook and loop fasteners, mushroom fasteners, snaps, pins, belts and the like, and combinations thereof. For example, the fasteners 62 may be hook type fasteners and the outer cover 42 or attachment panel 66 may be configured to function as a complimentary loop type fastener. Desirably, the fasteners 62 are hook type fasteners which are refastenably engageable directly with the outer cover 42. Such an arrangement provides the ability to vary the size of the waist opening in very small increments over a wide range to fit the waist of the wearer.

The different aspects of the present invention advantageously provide pant-like, refastenable disposable absorbent articles which include the combination of releasable joints and refastenable fasteners. The side panels are releasably prefastened to allow the absorbent article to be pulled up or down over the hips of the wearer such as conventional training pants. Moreover, the fasteners can be used to refastenably engage and adjust the front and back waist portions of the absorbent article to maintain the absorbent article about the waist of the wearer after the article has been pulled on in a similar manner to conventional diapers. Further, the diaper is provided in the pant-like prefastened configuration using long releasable joints for improved effectiveness, while the distal edge of the fasteners are proportioned to be smaller in length to allow improved mobility with less irritation and red marking. The releasable joints, maintain the article in a prefastened condition as the article is pulled up or down over the hips of the wearer. Moreover, in such a configuration, the releasable joints may prevent movement and shifting of the waist portions relative to each other for improved manufacturability, fit and performance. The releasable bonds also prevent the rollover or folding in of the side and waist edges of the prefastened absorbent article as it is pulled over the wearer's hips.

As a result, the absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness. Further, due to the releasable joint and a longitudinally smaller fastener, the present invention may be used in the pant-like configuration or the conventional configuration while providing the wearer with improved fit and comfort.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. A pant-like, refastenable, disposable absorbent article which defines a front waist region, a back waist region, a crotch region which extends between and connects the waist regions, a longitudinal direction and a lateral direction, the absorbent article comprising:
   a) an absorbent chassis that includes a pair of laterally opposed side edges and a pair of longitudinally opposed waist edges;
   b) a pair of opposed back panels which are permanently attached to the side edges of the absorbent chassis in the back waist region of the absorbent article;
   c) a pair of opposed front panels which are releasably attached to the side edges of the absorbent chassis in the front waist region of the absorbent article to provide a pair of releasable joints wherein the front panel and the back panel on each side edge of the absorbent chassis are connected together along a side seam; and
   d) a fastener permanently attached to each of the front panels configured to engage an exterior surface of the absorbent chassis in the front waist region, wherein each releasable joint is provided by the fastener and one or more releasable bonds, wherein the one or more releasable bonds becomes destroyed upon first disengagement and the releasable joint can be broken without tearing the side panels.

2. The absorbent article of claim 1 wherein the absorbent chassis comprises:
   a) an outer cover;
   b) a bodyside liner which is connected to the outer cover in a superposed relation; and
   c) an absorbent core disposed between the outer cover and the bodyside liner.

3. The absorbent article of claim 1 wherein the fasteners are hook and loop type fasteners.

4. The absorbent article of claim 1 and further comprising at least one attachment panel which is located on an exterior surface of the absorbent chassis wherein the fasteners are refastenably engaged to the attachment panel.

5. The absorbent article of claim 1 wherein the absorbent chassis includes an outer cover which provides the exterior surface of the absorbent chassis and wherein the fasteners are configured to refastenably engage directly with the outer cover of the absorbent chassis.

6. The absorbent article of claim 1 wherein the pair of opposed back panels and the pair of opposed front panels are stretchable in at least the lateral direction.

7. The absorbent article of claim 1 and further defining an article centerline in the longitudinal direction wherein each of the fasteners includes a fastener ear that is attached the font panel and extends inwardly toward the article centerline.

8. The absorbent article of claim 7 wherein each of the fastener ears are stretchable in at least the lateral direction.

* * * * *